United States Patent [19]

DeCoster

[11] Patent Number: Plant 6,086

[45] Date of Patent: Jan. 19, 1988

[54] PHILODENDRON PLANT NAMED IMPERIAL GREEN

[76] Inventor: Paul DeCoster, Brusselsesteenweg 94, 9230 Melle, Belgium

[21] Appl. No.: 813,926

[22] Filed: Dec. 27, 1985

[51] Int. Cl.[4] ..... A01H 5/00

[52] U.S. Cl. ..... Plt./88

[58] Field of Search ..... Plt./88

*Primary Examiner*—Robert E. Bagwill

*Attorney, Agent, or Firm*—Schwartz, Jeffery, Schwaab, Mack, Blumenthal & Evans

[57] ABSTRACT

A philodendron plant named Imperial Green having rosette plant form; dark, relatively large foliage; ease of propagation by tissue culture; compact growth habit both in 4" and larger pots; close symmetrical internodes, and a fast growth habit.

2 Drawing Figures

1

The present invention comprises a new and distinct cultivar of philodendron plant named Imperial Green.

The new cultivar was discovered growing among several hundred random seedlings obtained in approximately September of 1977 from Bamboo Nursery, Opapka, Fla. The plants were approximately 3–4" long with roots, but not rooted in soil, and were indistinguishable one from the other at the time of purchase. The parentage of the new cultivar was not known at the time of acquisition, nor is it now known.

When the seedlings were grown to mature plants by applicant in Melle, Belgium, in the greenhouses of applicant, the novel characteristics of the new cultivar were readily evident. Asexual reproduction by me of the new cultivar by tissue culture beginning in approximately 1982 in Melle, Belgium, and repeated asexual reproduction thereafter, has demonstrated that Imperial Green retains its distinctive characteristics through successive propagation.

The following characteristics in combination distinguish Imperial Green from other philodendron cultivars of this general type.

1. A rosette plant form, i.e. self-heading from which leaf stalks develop, in much the same manner as in the cultivar Black Cardinal, disclosed in U.S. Plant Pat. No. 5,355, or the commercial cultivar Pluto.

2. Dark green, relatively large foliage.

3. Propagates very efficiently by tissue culture, a very important characteristic for rosette type philodendrons. The more compact form of rosette types, as compared to the more vertically grown philodendron normally attached to moss poles or the like, makes removal of the meristem difficult. In Imperial Green, such removal can be accomplished relatively easily.

4. Compact growth habit and form, from beginning to maturity, thereby allowing plant to be sold in 4" pots and larger with the same degree of compactness. It is therefore excellent for indoor decorating and outdoor planting.

5. Very close and symmetrical internodes, approximately 1 cm apart, thereby providing the compact form indicated.

6. Fast grower for rosette type, reaching approximately 30–33" in diameter and two (2) feet above edge of 25 cm pot in approximately 10 months, starting from a 10 cm plantlet obtained from tissue culture.

2

7. In immature plants (plant prior to flowering), leaves are relatively erect and carried on rigid stalks thereby making the plant convenient to wrap and ship.

8. The sheathing around the petioles is an attractive rose-pink on the exterior to a light yellow-buff on the inner surface.

9. The buds are oblong and generally red-purple in color. When opening the outside of the spathe retain the bud color, and the inside of the spathe ranges from light to dark pink. This provides a pleasant contrast with the spadix, which is normally white.

10. The edges of the leaves have a clearly visible but very narrow band, less than 1 mm, around the entire edge, with the band appearing to be translucent.

In the color photographic drawings, sheet 1 is a top perspective view of a plant of Imperial Green, approximately ten (10) months old.

Sheet 2 is a side elevational view of the same plant, showing more clearly the compact, rosette form. The photographs were taken when the plant was not in flower.

The following observations and measurements are based on plants of Imperial Green ten (10) months in age grown in Melle, Belgium in greenhouses in accordance with standard commercial practices. Color values are based on The Royal Horticultural Society Colour Chart (R.H.S.) with the color values being taken in November at approximately 2:00 p.m. under natural light conditions.

FORM CHARACTERISTICS

Leaf shape:

*Mature.*—Generally elliptic, with bottom of leaf being concavely shaped at petiole connecter; undulating or wavy in direction of length, particularly at edge.

*Immature.*—Generally ovate, with bottom of leaf at petiole connecter being essentially a continuous edge.

*Tip.*—Cuspidate.

*Base.*—Concavely shaped relative to rib; sagittate.

*Margin.*—Smooth, with the edges of the leaves having a very narrow but visible band (less than 1 mm) around the entire edge.

*Veination.*—Present.

Leaf attachment: Stalked.

Leaf arrangement: Alternate.

Petiole: Rigid, extending generally more vertical than horizontal in center of plant; round except flat on inner surface.

Stem: rosette type, short, heavy internodes ½" to 1".

Overall appearance: Self-branching, free standing, open but compact.

SIZE CHARACTERISTICS OF TYPICAL COMMERCIAL PLANT

Leaf:

*Width at widest point.*—21–22 cm.

*Width 1" from top.*—7 cm.

*Length.*—34–35 cm.

Petiole:

*Length.*—25 cm for mature leaves.

*Diameter (center).*—Approximately 1.5 cm.

*Internode spacing.*—1 cm.

Stem diameter: Approximately 3–4 cm.

COLOR CHARACTERISTICS

Leaf:

*Mature.*—Top approximately 147A; under surface 144A.

*Immature.*—Top 144A when first unfolding on both top and bottom, gradually darkening to mature colors indicated.

*Veination.*—Midrib, 147B; veins, 147A.

Stem: 147B.

Petiole: 147A–B, with dark, fine and short striations on both round outer and flat inner surfaces; sheath around petiole varies greatly in exterior color, ranging from approximately 35B–D for immature petioles to 146A–D prior to dropping from emerging petiole.

I claim

1. A new and distinct cultivar of philodendron plant named Imperial Green, as illustrated and described, and particularly characterized by the combined features of rosette plant form; dark, relatively large foliage; ease of propagation by tissue culture; compact growth habit, both in 4" and larger pots; close, symmetrical internodes, and fast growth habit.

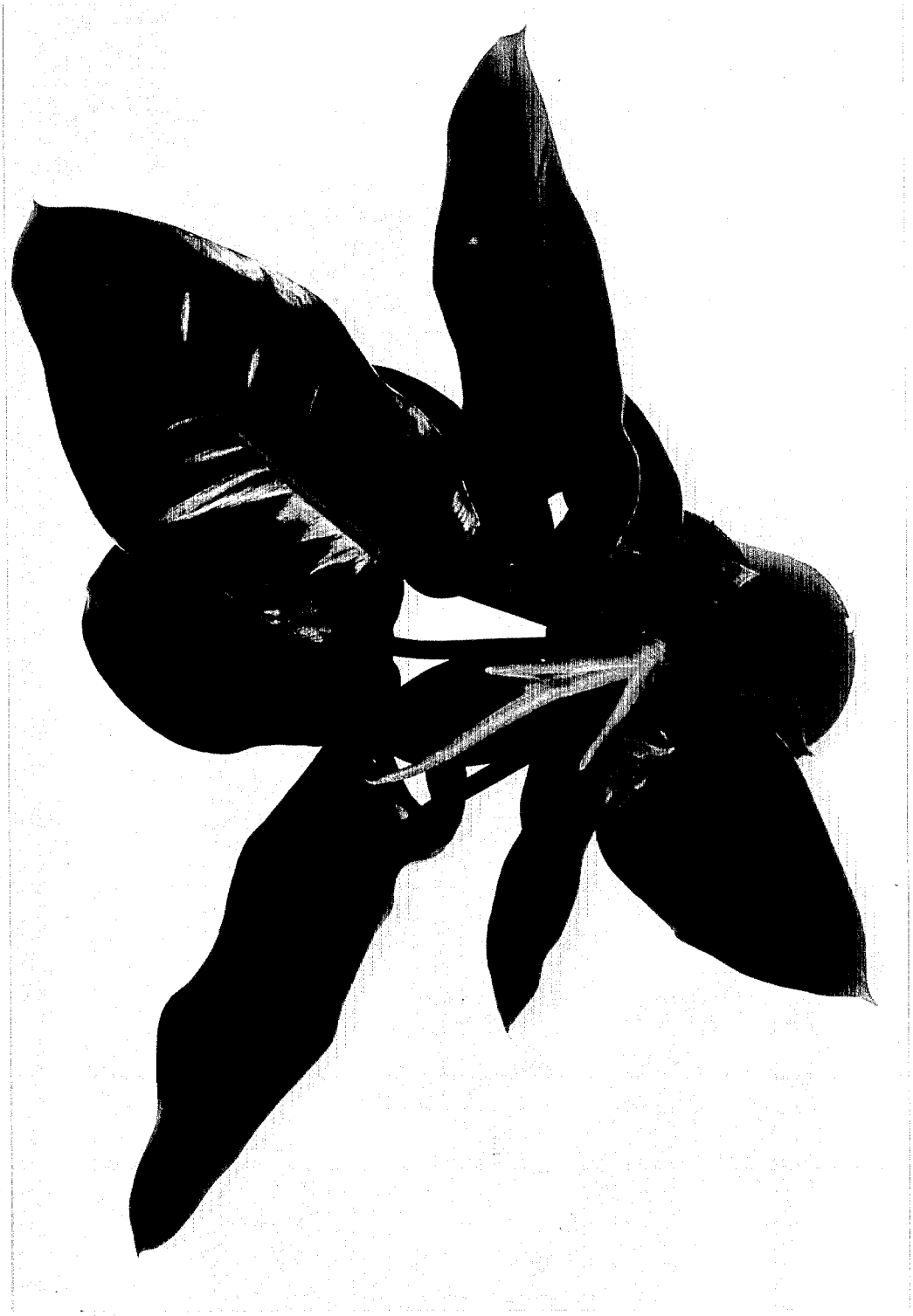

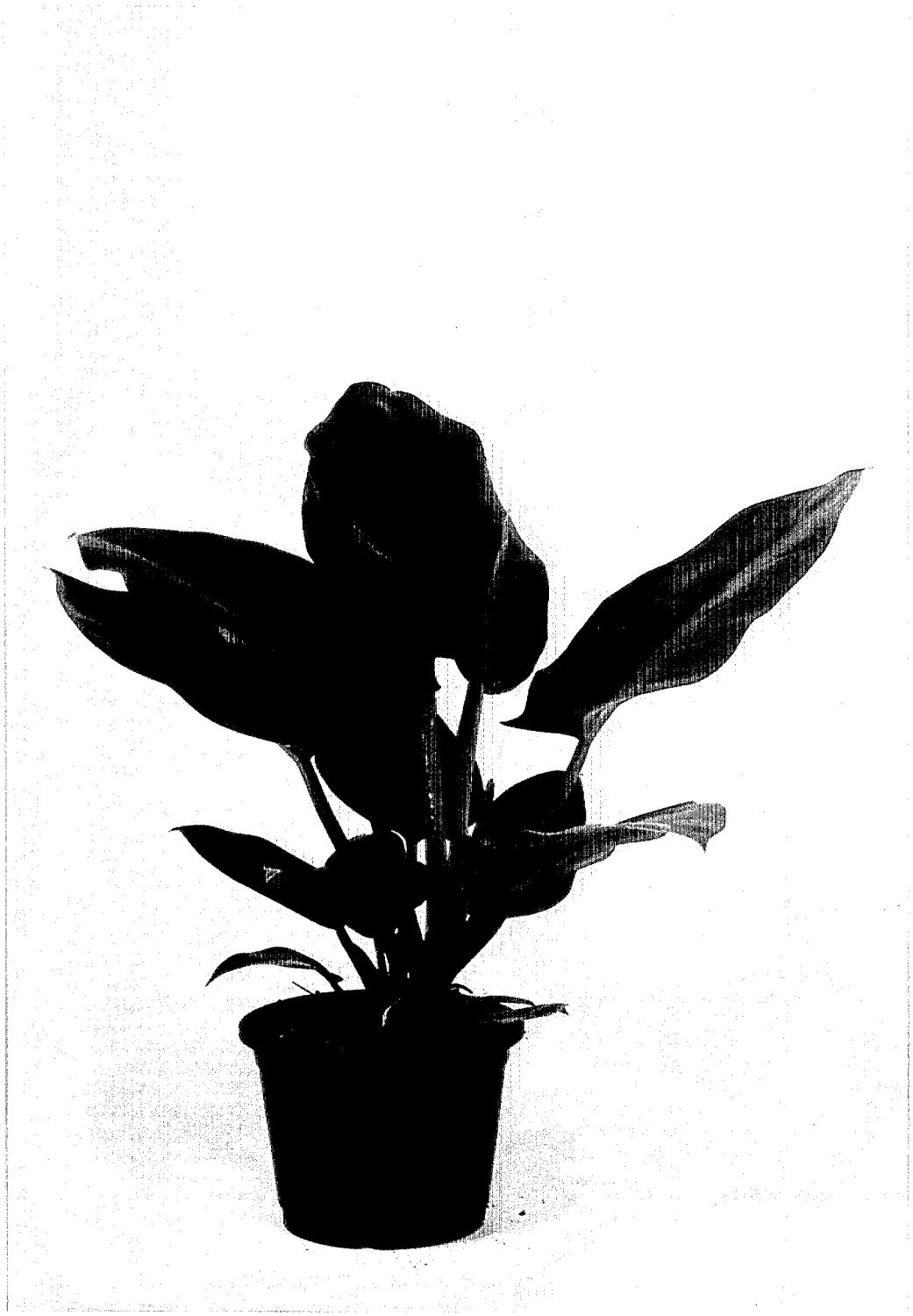

* * * * *